(12) United States Patent
Hale et al.

(10) Patent No.: US 7,018,621 B2
(45) Date of Patent: *Mar. 28, 2006

(54) DELIVERY OF RIZATRIPTAN OR ZOLMITRIPTAN THROUGH AN INHALATION ROUTE

(75) Inventors: Ron L. Hale, Woodside, CA (US); Joshua D. Rabinowitz, Mountain View, CA (US); Dennis W. Solas, San Francisco, CA (US); Alejandro C. Zaffaroni, Atherton, CA (US)

(73) Assignee: Alexza Pharmaceuticals, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/792,012

(22) Filed: Mar. 3, 2004

(65) Prior Publication Data

US 2004/0170570 A1 Sep. 2, 2004

Related U.S. Application Data

(63) Continuation of application No. 10/155,621, filed on May 22, 2002, now Pat. No. 6,759,029.

(60) Provisional application No. 60/332,280, filed on Nov. 21, 2001, provisional application No. 60/336,218, filed on Oct. 30, 2001, provisional application No. 60/317,479, filed on Sep. 5, 2001, provisional application No. 60/294,203, filed on May 24, 2001.

(51) Int. Cl.
 A61K 9/12 (2006.01)
 A61K 9/14 (2006.01)
 A61M 15/00 (2006.01)

(52) U.S. Cl. .......................... 424/45; 424/46; 424/489; 424/499; 128/200.14; 128/200.24; 514/958

(58) Field of Classification Search ................ 424/45, 424/46, 43, 434, 489, 499; 514/220, 414, 514/958; 128/200.14, 200.24
See application file for complete search history.

(56) References Cited

U.S. PATENT DOCUMENTS

| 3,219,533 A | 11/1965 | Mullins |
| 3,560,607 A | 2/1971 | Hartley et al. |
| 3,949,743 A | 4/1976 | Shanbrom |
| 3,982,095 A | 9/1976 | Robinson |
| 4,141,369 A | 2/1979 | Burruss |
| RE30,285 E | 5/1980 | Babington |
| 4,303,083 A | 12/1981 | Burruss, Jr. |
| 4,474,191 A | 10/1984 | Steiner |
| 4,484,576 A | 11/1984 | Albarda |
| 4,566,451 A | 1/1986 | Badewien |
| 4,708,151 A | 11/1987 | Shelar |
| 4,734,560 A | 3/1988 | Bowen |
| 4,735,217 A | 4/1988 | Gerth et al. |
| 4,819,665 A | 4/1989 | Roberts et al. |
| 4,848,374 A | 7/1989 | Chard et al. |
| 4,853,517 A | 8/1989 | Bowen et al. |
| 4,895,719 A | 1/1990 | Radhakrishnan et al. |
| 4,906,417 A | 3/1990 | Gentry |
| 4,917,119 A | 4/1990 | Potter et al. |
| 4,924,883 A | 5/1990 | Perfetti et al. |
| 4,941,483 A | 7/1990 | Ridings et al. |
| 4,963,289 A | 10/1990 | Ortiz et al. |
| 5,042,509 A | 8/1991 | Banerjee et al. |
| 5,049,389 A | 9/1991 | Radhakrishnan |
| 5,060,671 A | 10/1991 | Counts et al. |
| 5,099,861 A | 3/1992 | Clearman et al. |
| 5,135,009 A | 8/1992 | Muller et al. |
| 5,144,962 A | 9/1992 | Counts et al. |
| 5,146,915 A | 9/1992 | Montgomery |
| 5,224,498 A | 7/1993 | Deevi et al. |
| 5,345,951 A | 9/1994 | Serrano et al. |
| 5,366,770 A | 11/1994 | Wang |
| 5,388,574 A | 2/1995 | Ingebrethsen |
| 5,456,247 A | 10/1995 | Shilling et al. |
| 5,511,726 A | 4/1996 | Greenspan et al. |
| 5,544,646 A | 8/1996 | Lloyd et al. |
| 5,564,442 A | 10/1996 | MacDonald et al. |

(Continued)

FOREIGN PATENT DOCUMENTS

EP 0 358 114 3/1990

(Continued)

OTHER PUBLICATIONS

U.S. Appl. No. 10/633,876, filed Aug. 4, 2003, Hale et al.

(Continued)

*Primary Examiner*—Sreeni Padmanabhan
*Assistant Examiner*—Mina Haghighatian
(74) *Attorney, Agent, or Firm*—Swanson & Bratschun, LLC; William L. Leschensky

(57) ABSTRACT

The present invention relates to the delivery of compounds for the treatment of migraine and headache through an inhalation route. Specifically, it relates to aerosols containing rizatriptan or zolmitriptan that are used in inhalation therapy. In a method aspect of the present invention, rizatriptan or zolmitriptan is administered to a patient through an inhalation route. The method comprises: a) heating a thin layer of rizatriptan or zolmitriptan on a solid support to form a vapor; and, b) passing air through the heated vapor to produce aerosol particles having less than 5% drug degradation products. In a kit aspect of the present invention, a kit for delivering rizatriptan or zolmitriptan through an inhalation route is provided which comprises: a) a thin coating of a rizatriptan or zolmitriptan composition; and, b) a device for dispensing said thin coating as a condensation aerosol.

8 Claims, 1 Drawing Sheet

U.S. PATENT DOCUMENTS

| | | | |
|---|---|---|---|
| 5,592,934 | A | 1/1997 | Thwaites |
| 5,605,146 | A | 2/1997 | Sarela |
| 5,649,554 | A | 7/1997 | Sprinkel et al. |
| 5,666,977 | A | 9/1997 | Higgins et al. |
| 5,694,919 | A | 12/1997 | Rubsamen et al. |
| 5,735,263 | A | 4/1998 | Rubsamen et al. |
| 5,738,865 | A | 4/1998 | Baichwal et al. |
| 5,743,251 | A | 4/1998 | Howell et al. |
| 5,758,637 | A | 6/1998 | Ivri et al. |
| 5,767,117 | A | 6/1998 | Moskowitz |
| 5,819,756 | A | 10/1998 | Mielordt |
| 5,840,246 | A | 11/1998 | Hammons et al. |
| 5,855,913 | A | 1/1999 | Hanes et al. |
| 5,874,481 | A | 2/1999 | Weers et al. |
| 5,894,841 | A | 4/1999 | Voges |
| 5,915,378 | A | 6/1999 | Lloyd et al. |
| 5,918,595 | A | 7/1999 | Olsson et al. |
| 5,934,272 | A | 8/1999 | Lloyd et al. |
| 5,957,124 | A | 9/1999 | Lloyd et al. |
| 5,960,792 | A | 10/1999 | Lloyd et al. |
| 5,993,805 | A | 11/1999 | Sutton et al. |
| 6,041,777 | A | 3/2000 | Faithfull et al. |
| 6,051,566 | A | 4/2000 | Bianco |
| 6,090,212 | A | 7/2000 | Mahawili |
| 6,095,134 | A | 8/2000 | Sievers et al. |
| 6,095,153 | A | 8/2000 | Kessler et al. |
| 6,102,036 | A | 8/2000 | Slutsky et al. |
| 6,131,570 | A | 10/2000 | Schuster et al. |
| 6,136,295 | A | 10/2000 | Edwards et al. |
| 6,155,268 | A | 12/2000 | Takeuchi |
| 6,158,431 | A | 12/2000 | Poole |
| 6,234,167 | B1 | 5/2001 | Cox et al. |
| 6,241,969 | B1 | 6/2001 | Saidi et al. |
| 6,255,334 | B1 | 7/2001 | Sands |
| 6,306,431 | B1 | 10/2001 | Zhang et al. |
| 6,376,550 | B1 | 4/2002 | Raber et al. |
| 6,461,591 | B1 | 10/2002 | Keller et al. |
| 6,506,762 | B1 | 1/2003 | Horvath et al. |
| 6,514,482 | B1 | 2/2003 | Bartus et al. |
| 6,591,839 | B1 | 7/2003 | Meyer et al. |
| 6,632,047 | B1 | 10/2003 | Vinegar et al. |
| 6,701,922 | B1 | 3/2004 | Hindle et al. |
| 6,772,756 | B1 | 8/2004 | Shayan |
| 2001/0020147 | A1 | 9/2001 | Staniforth et al. |
| 2002/0037828 | A1 | 3/2002 | Wilson et al. |
| 2002/0058009 | A1 | 5/2002 | Bartus et al. |
| 2002/0086852 | A1 | 7/2002 | Cantor |
| 2002/0112723 | A1 | 8/2002 | Schuster et al. |
| 2002/0117175 | A1 | 8/2002 | Kottayil et al. |
| 2002/0176841 | A1 | 11/2002 | Barker et al. |
| 2003/0000518 | A1 | 1/2003 | Rabinowitz et al. |
| 2003/0004142 | A1 | 1/2003 | Prior et al. |
| 2003/0005924 | A1 | 1/2003 | Rabinowitz et al. |
| 2003/0005925 | A1 | 1/2003 | Hale et al. |
| 2003/0007933 | A1 | 1/2003 | Rabinowitz et al. |
| 2003/0007934 | A1 | 1/2003 | Rabinowitz et al. |
| 2003/0012737 | A1 | 1/2003 | Rabinowitz et al. |
| 2003/0012738 | A1 | 1/2003 | Rabinowitz et al. |
| 2003/0012740 | A1 | 1/2003 | Rabinowitz et al. |
| 2003/0015189 | A1 | 1/2003 | Rabinowitz et al. |
| 2003/0015190 | A1 | 1/2003 | Rabinowitz et al. |
| 2003/0015196 | A1 | 1/2003 | Hodges et al. |
| 2003/0017114 | A1 | 1/2003 | Rabinowitz et al. |
| 2003/0017115 | A1 | 1/2003 | Rabinowitz et al. |
| 2003/0017116 | A1 | 1/2003 | Rabinowitz et al. |
| 2003/0017117 | A1 | 1/2003 | Rabinowitz et al. |
| 2003/0017118 | A1 | 1/2003 | Rabinowitz et al. |
| 2003/0017119 | A1 | 1/2003 | Rabinowitz et al. |
| 2003/0017120 | A1 | 1/2003 | Rabinowitz et al. |
| 2003/0021753 | A1 | 1/2003 | Rabinowitz et al. |
| 2003/0021754 | A1 | 1/2003 | Rabinowitz et al. |
| 2003/0021755 | A1 | 1/2003 | Hale et al. |
| 2003/0032638 | A1 | 2/2003 | Kim et al. |
| 2003/0035776 | A1 | 2/2003 | Hodges et al. |
| 2003/0062042 | A1 | 4/2003 | Wensley et al. |
| 2003/0091511 | A1 | 5/2003 | Rabinowitz et al. |
| 2003/0138382 | A1 | 7/2003 | Rabinowitz |
| 2003/0206869 | A1 | 11/2003 | Rabinowitz et al. |
| 2003/0209240 | A1 | 11/2003 | Hale et al. |
| 2004/0009128 | A1 | 1/2004 | Rabinowitz et al. |
| 2004/0016427 | A1 | 1/2004 | Byron et al. |
| 2004/0096402 | A1 | 5/2004 | Hodges et al. |
| 2004/0099269 | A1 | 5/2004 | Hale et al. |
| 2004/0101481 | A1 | 5/2004 | Hale et al. |
| 2004/0105818 | A1 | 6/2004 | Hale et al. |
| 2004/0105819 | A1 | 6/2004 | Hale et al. |
| 2004/0126326 | A1 | 7/2004 | Rabinowitz et al. |
| 2004/0126327 | A1 | 7/2004 | Rabinowitz et al. |
| 2004/0126328 | A1 | 7/2004 | Rabinowitz et al. |
| 2004/0126329 | A1 | 7/2004 | Rabinowitz et al. |
| 2004/0127481 | A1 | 7/2004 | Rabinowitz et al. |
| 2004/0127490 | A1 | 7/2004 | Rabinowitz et al. |
| 2004/0156788 | A1 | 8/2004 | Rabinowitz et al. |
| 2004/0156789 | A1 | 8/2004 | Rabinowitz et al. |
| 2004/0156790 | A1 | 8/2004 | Rabinowitz et al. |
| 2004/0156791 | A1 | 8/2004 | Rabinowitz et al. |

FOREIGN PATENT DOCUMENTS

| | | |
|---|---|---|
| EP | 1 080 720 | 7/2001 |
| EP | 0 606 486 | 8/2001 |
| GB | 502 761 | 3/1939 |
| WO | WO 94/09842 | 5/1994 |
| WO | WO 96/09846 | 4/1996 |
| WO | WO 96/13161 | 5/1996 |
| WO | WO 96/13290 | 5/1996 |
| WO | WO 96/13291 | 5/1996 |
| WO | WO 96/13292 | 5/1996 |
| WO | WO 96/30068 | 10/1996 |
| WO | WO 97/27804 | 8/1997 |
| WO | WO 97/36574 | 10/1997 |
| WO | WO 98/02186 | 1/1998 |
| WO | WO 98/16205 | 4/1998 |
| WO | WO 98/22170 | 5/1998 |
| WO | WO 98/31346 | 7/1998 |
| WO | WO 98/34595 | 8/1998 |
| WO | WO 98/36651 | 8/1998 |
| WO | WO 99/16419 | 4/1999 |
| WO | WO 99/64094 | 12/1999 |
| WO | WO 00/00176 | 1/2000 |
| WO | WO 00/00215 | 1/2000 |
| WO | WO 00/27363 | 5/2000 |
| WO | WO 00/29053 | 5/2000 |
| WO | WO 00/47203 | 9/2000 |
| WO | WO 00/64940 | 11/2000 |
| WO | WO 00/66084 | 11/2000 |
| WO | WO 00/66206 | 11/2000 |
| WO | WO 00/76673 | 12/2000 |
| WO | WO 01/05459 | 1/2001 |
| WO | WO 01/13957 | 3/2001 |
| WO | WO 01/17568 | 3/2001 |
| WO | WO 01/95903 | 12/2001 |
| WO | WO 02/00198 | 1/2002 |
| WO | WO 02/24158 | 3/2002 |
| WO | WO 03/37412 | 5/2003 |

OTHER PUBLICATIONS

U.S. Appl. No. 10/633,877, filed Aug. 4, 2003, Hale et al.
U.S. Appl. No. 10/749,537, filed Dec. 30, 2003, Rabinowitz et al.
U.S. Appl. No. 10/749,539, filed Dec. 30, 2003, Rabinowitz et al.

U.S. Appl. No. 10/766,149, filed Jan. 27, 2004, Rabinowitz et al.
U.S. Appl. No. 10/766,279, filed Jan. 27, 2004, Rabinowitz et al.
U.S. Appl. No. 10/766,566, filed Jan. 27, 2004, Rabinowitz et al.
U.S. Appl. No. 10/766,574, filed Jan. 27, 2004, Rabinowitz et al.
U.S. Appl. No. 10/766,634, filed Jan. 27, 2004, Rabinowitz et al.
U.S. Appl. No. 10/766,647, filed Jan. 27, 2004, Rabinowitz et al.
U.S. Appl. No. 10/767,115, filed Jan. 28, 2004, Rabinowitz et al.
U.S. Appl. No. 10/768,205, filed Jan. 29, 2004, Rabinowitz et al.
U.S. Appl. No. 10/768,220, filed Jan. 29, 2004, Rabinowitz et al.
U.S. Appl. No. 10/768,281, filed Jan. 29, 2004, Rabinowitz et al.
U.S. Appl. No. 10/768,293, filed Jan. 29, 2004, Rabinowitz et al.
U.S. Appl. No. 10/769,046, filed Jan. 30, 2004, Rabinowitz et al.
U.S. Appl. No. 10/769,051, filed Jan. 30, 2004, Rabinowitz et al.
U.S. Appl. No. 10/769,157, filed Jan. 29, 2004, Rabinowitz et al.
U.S. Appl. No. 10/769,197, filed Jan. 29, 2004, Rabinowitz et al.
U.S. Appl. No. 10/775,583, filed Feb. 9, 2004, Rabinowitz et al.
U.S. Appl. No. 10/775,586, filed Feb. 9, 2004, Rabinowitz et al.
U.S. Appl. No. 10/791,915, filed Mar. 3, 2004, Hale et al.
U.S. Appl. No. 10/792,001, filed Mar. 3, 2004, Rabinowitz et al.
U.S. Appl. No. 10/792,013, filed Mar. 3, 2004, Rabinowitz et al.
U.S. Appl. No. 10/792,096, filed Mar. 3, 2004, Hale et al.
U.S. Appl. No. 10/792,239, filed Mar. 3, 2004, Hale et al.
U.S. Appl. No. 10/813,721, filed Mar. 31, 2004, Rabinowitz et al.
U.S. Appl. No. 10/813,722, filed Mar. 31, 2004, Rabinowitz et al.
U.S. Appl. No. 10/814,690, filed Mar. 31, 2004, Rabinowitz et al.
U.S. Appl. No. 10/814,998, filed Mar. 31, 2004, Rabinowitz et al.
U.S. Appl. No. 10/815,527, filed Apr. 1, 2004, Rabinowitz et al.
U.S. Appl. No. 10/816,407, filed Apr. 1, 2004, Rabinowitz et al.
U.S. Appl. No. 10/816,492, filed Apr. 1, 2004, Rabinowitz et al.
U.S. Appl. No. 10/816,567, filed Apr. 1, 2004, Rabinowitz et al.
U.S. Appl. No. 10/912,462, filed Aug. 4, 2004, Hale et al.
Bennett, R. L. et al. (1981). "Patient-Controlled Analgesia: A New Concept of Postoperative Pain Relief," *Annual Surg*. 195(6):700-705.
Carroll, M.E. et al. (1990), "Cocaine-Base Smoking in Rhesus Monkey: Reinforcing and Physiological Effects," Psychopharmacology (Berl) 102:443-450.

Clark, A. and Byron, P. (1986). "Dependence of Pulmonary Absorption Kinetics on Aerosol Particle Size," *Z. Erkrank*. 166:13-24.
Darquenne, C. et al. (1997). "Aerosol Dispersion in Human Lung: Comparison Between Numerical Simulations and Experiments for Bolus Tests," *American Physiological Society*. 966-974.
Davies, C. N. et al. (May 1972). "Breathing of Half-Micron Aerosols," *Journal of Applied Physiology*. 32(5):591-600.
Dershwitz, M., M.D., et al. (Sep. 2000). "Pharmacokinetics and Pharmacodynamics of Inhaled versus Intravenous Morphine in Healthy Volunteers," *Anesthesiology*. 93(3): 619-628.
Finlay, W. H. (2001). "The Mechanics of Inhaled Pharmaceutical Aerosols", Academic Press: San Diego Formula 2.39. pp. 3-14 (Table of Contents). pp. v-viii.
Gonda, I. (1991). "Particle Deposition in the Human Respiratory Tract,"Chapter 176, *The Lung: Scientific Foundations*. Crystal R.G.and West, J.B. (eds.), Raven Publishers, New York. pp. 2289-2294.
Hatsukami D., et al. (May 1990) "A Method for Delivery of Precise Doses of Smoked Cocaine-Base to Human." *Pharmacology Biochemistry & Behavior*. 36(1):1-7.
Heyder, J. et al. (1986). "Deposition of Particles in the Human Respiratory Tract in the Size Range 0.005-15 µm," *J. Aerosol Sci*. 17(5):811-822.
Huizer, H. (1987). "Analytical Studies on Illicit Heron. V. Efficacy of Volitization During Heroin Smoking." *Pharmaceutisch Weekblad Scientific Edition*. 9(4):203-211.
Hurt, R. D., MD and Robertson, C. R., PhD, (Oct. 1998). "Prying Open the Door to the Tobacco Industry's Secrets About Nicotine: The Minnesota Tobacco Trial," *JAMA* 280 (13):1173-1181.
Lichtman, A. H. et al. (1996). "Inhalation Exposure to Volatilized Opioids Produces Antinociception in Mice," *Journal of Pharmacology and Experimental Therapeutics*. 279(1):69-76 XP-001118649.
Martin, B. R. and Lue, L. P. (May/Jun. 1989). "Pyrolysis and Volatilization of Cocaine," *Journal of Analytical Toxicology* 13:158-162.
Mattox, A.J. and Carroll, M.E. (1996). "Smoked Heroin Self-Administration in Rhesus Monkeys," *Psychopharmacology* 125:195-201.
Meng, Y. et al. (1997). "Inhalation Studies with Drugs of Abuse", *NIDA Research Monogragh* 173:201-224.
Meng, Y., et al. (1999). "Pharmacological effects of methamphetamine and other stimulants via inhalation exposure," *Drug and Alcohol Dependence*. 53:111-120.
Office Action mailed Aug. 13, 2003 for U.S. Appl. No. 10/153,313 filed May 21, 2002 "Delivery of Benzodiazepines Through an Inhalation Route".
Pankow, J. F. et al. (1997). "Conversion of Nicotine in Tobacco Smoke to Its Volatile and Available Free-Base Form through the Action of Gaseous Ammonia," *Environ. Sci. Technol*. 31:2428-2433.
Pankow, J. (Mar. 2000). ACS Conference-San Francisco-Mar. 26, 2000. Chemistry of Tobacco Smoke. pp. 1-8.
Seeman, J. et al. (1999). "The Form of Nicotine in Tobacco. Thermal Transfer of Nicotine and Nicotine Acid Salts to Nicotine in the Gas Phase," *J. Agric. Food Chem*. 47(12): 5133-5145.
Sekine, H. and Nakahara, Y. (1987). "Abuse of Smoking Methamphetamine Mixed with Tobacco: 1. Inhalation Efficiency and Pyrolysis Products of Methamphetamine," *Journal of Forensic Science* 32(5):1271-1280.

Vapotronics, Inc. (1998) located at <http://www.vapotronics.com.au/banner.htm.>, 11 pages, (visited on Jun. 5, 2000).

Ward, M. E. MD, et al. (Dec. 1997). "Morphine Pharmacokinetics after Pulmonary Administration from a Novel Aerosol Delivery System," *Clinical Pharmocology & Therapeutics* 62(6):596-609.

Wood, R. W. et al. (1996). "Generation of Stable Test Atmospheres of Cocaine Base and Its Pyrolyzate, Methylecgonidine, and Demonstration of Their Biological Activity." *Pharmacology Biochemistry & Behavior*. 55(2):237-248.

U.S. Appl. No. 10/057,198, filed Oct. 26, 2001, Lloyd et al.
U.S. Appl. No. 10/146,088, filed May 13, 2002, Hale et al.
U.S. Appl. No. 10/280,315, filed Oct. 25, 2002, Shen.
U.S. Appl. No. 10/302,614, filed Nov. 21, 2002, Lu.
U.S. Appl. No. 10/322,227, filed Dec. 17, 2002, Novack et al.
U.S. Appl. No. 10/442,385, filed May 20, 2003, Cross et al.
U.S. Appl. No. 10/719,540, filed Nov. 20, 2003, Hale et al.
U.S. Appl. No. 10/750,303, filed Dec. 30, 2003, Rabinowitz et al.
U.S. Appl. No. 10/850,895, filed May 20, 2004, Damani et al.
U.S. Appl. No. 10/851,018, filed May 20, 2004, Hale et al.
U.S. Appl. No. 10/851,429, filed May 20, 2004, Hale et al.
U.S. Appl. No. 10/851,432, filed May 20, 2004, Hale et al.
U.S. Appl. No. 10/851,883, filed May 20, 2004, Hale et al.
U.S. Appl. No. 10/861,554, filed Jun. 3, 2004, Cross et al.
U.S. Appl. No. 10/912,417, filed Aug. 4, 2004, Bennett et al.
U.S. Appl. No. 10/917,720, filed Aug. 12, 2004, Hale et al.
U.S. Appl. No. 10/917,735, filed Aug. 12, 2004, Hale et al.

Office Action mailed Dec. 4, 2003 for U.S. Appl. No. 10/057,198 filed Oct. 26, 2001, "Method And Device For Delivering A Physiologically Active Compound".

Office Action mailed Jan. 12, 2005 for U.S. Appl. No. 10/057,197 filed Oct. 26, 2001, "Aerosol Generating Device And Method".

Office Action mailed Jun. 3, 2004 for U.S. Appl. No. 10/057,197 filed Oct. 26, 2001, "Aerosol Generating Device And Method".

Office Action mailed Dec. 15, 2003 for U.S. Appl. No. 10/057,197 filed Oct. 26, 2001, "Aerosol Generating Device And Method".

Office Action mailed Feb. 27, 2004 for U.S. Appl. No. 10/146,080 filed May 13, 2002, "Aerosol Forming Device For Use In Inhalation Therapy".

DELIVERY OF RIZATRIPTAN OR ZOLMITRIPTAN THROUGH AN INHALATION ROUTE

This application is a continuation of U.S. patent application Ser. No. 10/155,621, entitled "Delivery of Rizatriptan or Zolmitriptan Through an Inhalation Route," filed May 22, 2002 now U.S. Pat. No. 6,759,029, Hale, Rabinowitz, Solas, and Zaffaroni; which claims priority to U.S. provisional application Ser. No. 60/294,203 entitled "Thermal Vapor Delivery of Drugs," filed May 24, 2001, Rabinowitz and Zaffaroni; to U.S. provisional application Ser. No. 60/317,479 entitled "Aerosol Drug Delivery," filed Sep. 5, 2001, Rabinowitz and Zaffaroni; U.S. provisional application Ser. No. 60/332,280 entitled "Delivery of Rizatriptan or Zolmitriptan Through an Inhalation Route," filed Nov. 21, 2001, Rabinowitz and Hale; and to U.S. provisional application Ser. No. 60/336,218 entitled "Delivery of Rizatriptan or Zolmitriptan Through an Inhalation Route," filed Oct. 30, 2001, Rabinowitz and Hale; the entire disclosures of which are hereby incorporated by reference.

FIELD OF THE INVENTION

The present invention relates to the delivery of rizatriptan or zolmitriptan through an inhalation route. Specifically, it relates to aerosols containing rizatriptan or zolmitriptan that are used in inhalation therapy.

BACKGROUND OF THE INVENTION

There are a number of compositions currently marketed for the treatment of migraine headaches. The compositions contain at least one active ingredient that provides for observed therapeutic effects. Among the active ingredients given in such anti-migraine compositions are rizatriptan and zolmitriptan.

It is desirable to provide a new route of administration for rizatriptan and zolmitriptan that rapidly produces peak plasma concentrations of the compounds. The provision of such a route is an object of the present invention.

SUMMARY OF THE INVENTION

New routes of administration for the compounds may increase the rate at which their peak plasma concentrations are reached. Such routes are provided herein.

The present invention relates to the delivery of rizatriptan or zolmitriptan through an inhalation route. Specifically, it relates to aerosols containing rizatritpan or zolmitriptan that are used in inhalation therapy.

In a composition aspect of the present invention, the aerosol comprises particles comprising at least 5 percent by weight of rizatriptan or zolmitriptan. Preferably, the particles comprise at least 10 percent by weight of rizatriptan or zolmitriptan. More preferably, the particles comprise at least 20 percent, 30 percent, 40 percent, 50 percent, 60 percent, 70 percent, 80 percent, 90 percent, 95 percent, 97 percent, 99 percent, 99.5 percent or 99.97 percent by weight of rizatriptan or zolmitriptan.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of rizatriptan or zolmitriptan degradation products. Preferably, the particles comprise less than 5 percent by weight of rizatriptan or zolmitriptan degradation products. More preferably, the particles comprise less than 2.5, 1, 0.5, 0.1 or 0.03 percent by weight of rizatriptan or zolmitriptan degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent by weight of water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the particles comprise rizatriptan, the particles comprise less than 5 percent by weight of rizatriptan N-oxide ($C_{15}H_{19}N_5O$, MW of 285.34). Preferably, the particles comprise less than 2.5 percent by weight of rizatriptan N-oxide. More preferably, the particles comprise less than 1, 0.5, 0.1 or 0.03 percent by weight of rizatriptan N-oxide.

Typically, where the particles comprise rizatriptan, the particles comprise less than 5 percent by weight of didehydro rizatriptan (removal of $H_2$, $C_{15}H_{17}N_5$, MW of 267.33). Preferably, the particles comprise less than 2.5 percent by weight of didehydro rizatriptan. More preferably, the particles comprise less than 1, 0.5, 0.1 or 0.03 percent by weight of didehydro rizatriptan.

Typically, where the particles comprise zolmitriptan, the particles comprise less than 5 percent by weight of zolmitriptan N-oxide. Preferably, the particles comprise less than 2.5 percent by weight of zolmitriptan N-oxide. More preferably, the particles comprise less than 1, 0.5, 0.1 or 0.03 percent by weight of zolmitriptan N-oxide.

Typically, where the particles comprise zolmitriptan, the particles comprise less than 5 percent by weight of didehydro zolmitriptan. Preferably, the particles comprise less than 2.5 percent by weight of didehydro zolmitriptan. More preferably, the particles comprise less than 1, 0.5, 0.1 or 0.03 percent by weight of didehydro zolmitriptan.

Typically, the aerosol has an inhalable aerosol drug mass density of between 0.25 mg/L and 40 mg/L. Preferably, the aerosol has an inhalable aerosol drug mass density of between 0.5 mg/L and 20 mg/L. More preferably, the aerosol has an inhalable aerosol drug mass density of between 0.5 mg/L and 10 mg/L.

Typically, the aerosol has an inhalable aerosol particle density greater than $10^6$ particles/mL. Preferably, the aerosol has an inhalable aerosol particle density greater than $10^7$ particles/mL or $10^8$ particles/mL.

Typically, the aerosol particles have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.5. Preferably, the geometric standard deviation is less than 3.0. More preferably, the geometric standard deviation is less than 2.5 or 2.0.

Typically, the aerosol is formed by heating a composition containing rizatriptan or zolmitriptan to form a vapor and subsequently allowing the vapor to condense into an aerosol.

In another composition aspect of the present invention, a dose form of an antimigraine compound is provided for the treatment of migraine, wherein the dose form comprises less than the typical oral dose of the antimigraine compound.

Typically, where the antimigraine compound is rizatriptan, the dose form comprises less than 4 mg of rizatriptan. Preferably, the dose form comprises less than 3.5 mg of rizatriptan. More preferably, the dose form comprises less than 3.0 or 2.5 mg of rizatriptan.

Typically, where the antimigraine compound is zolmitriptan, the dose form comprises less than 1 mg of zolmitriptan. Preferably, the dose form comprises less than 0.75 mg of zolmitriptan. More preferably, the dose form comprises less than 0.5 mg of zolmitriptan.

Typically, the dose form further comprises less than 90 percent by weight of water. Preferably, the dose form further comprises less than 80 percent by weight of water. More preferably, the dose form further comprises less than 70 percent, 60 percent, 50 percent, 40 percent, 30 percent, 20 percent, or 10 percent by weight of water.

Typically, the dose form further comprises less than 90 percent by weight of a pharmaceutically acceptable excipient. Preferably, the dose form further comprises less than 80 percent by weight of a pharmaceutically acceptable excipient. More preferably, the dose form further comprises less than 70 percent, 60 percent, 50 percent, 40 percent, 30 percent, 20 percent, or 10 percent by weight of a pharmaceutically acceptable excipient.

In a method aspect of the present invention, either rizatriptan or zolmitriptan is delivered to a mammal through an inhalation route. The method comprises: a) heating a composition, wherein the composition comprises at least 5 percent by weight of rizatriptan or zolmitriptan, to form a vapor; and, b) allowing the vapor to cool, thereby forming a condensation aerosol comprising particles, which is inhaled by the mammal. Preferably, the composition that is heated comprises at least 10 percent by weight of rizatriptan or zolmitriptan. More preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of rizatriptan or zolmitriptan.

Typically, the particles comprise at least 5 percent by weight of rizatriptan or zolmitriptan. Preferably, the particles comprise at least 10 percent by weight of rizatriptan or zolmitriptan. More preferably, the particles comprise at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of rizatritpan or zolmitriptan.

Typically, the aerosol has a mass of at least 10 µg. Preferably, the aerosol has a mass of at least 100 µg. More preferably, the aerosol has a mass of at least 200 µg.

Typically, the particles comprise less than 10 percent by weight of rizatriptan or zolmitriptan degradation products. Preferably, the particles comprise less than 5 percent by weight of rizatriptan or zolmitriptan degradation products. More preferably, the particles comprise 2.5, 1, 0.5, 0.1 or 0.03 percent by weight of rizatriptan or zolmitriptan degradation products.

Typically, the particles comprise less than 90 percent by weight of water. Preferably, the particles comprise less than 80 percent by weight of water. More preferably, the particles comprise less than 70 percent, 60 percent, 50 percent, 40 percent, 30 percent, 20 percent, 10 percent, or 5 percent water.

Typically, at least 50 percent by weight of the aerosol is amorphous in form, wherein crystalline forms make up less than 50 percent by weight of the total aerosol weight, regardless of the nature of individual particles. Preferably, at least 75 percent by weight of the aerosol is amorphous in form. More preferably, at least 90 percent by weight of the aerosol is amorphous in form.

Typically, where the particles comprise rizatriptan, the particles comprise less than 5 percent by weight of rizatriptan N-oxide ($C_{15}H_{19}N_5O$, MW of 285.34). Preferably, the particles comprise less than 2.5 percent by weight of rizatriptan N-oxide. More preferably, the particles comprise less than 1, 0.5, 0.1 or 0.03 percent by weight of rizatriptan N-oxide.

Typically, where the particles comprise rizatriptan, the particles comprise less than 5 percent by weight of didehydro rizatriptan (removal of $H_2$, $C_{15}H_{17}N_5$, MW of 267.33). Preferably, the particles comprise less than 2.5 percent by weight of didehydro rizatriptan. More preferably, the particles comprise less than 1, 0.5, 0.1 or 0.03 percent by weight of didehydro rizatriptan.

Typically, where the particles comprise zolmitriptan, the particles comprise less than 5 percent by weight of zolmitriptan N-oxide. Preferably, the particles comprise less than 2.5 percent by weight of zolmitriptan N-oxide. More preferably, the particles comprise less than 1, 0.5, 0.1 or 0.03 percent by weight of zolmitriptan N-oxide.

Typically, where the particles comprise zolmitriptan, the particles comprise less than 5 percent by weight of didehydro zolmitriptan. Preferably, the particles comprise less than 2.5 percent by weight of didehydro zolmitriptan. More preferably, the particles comprise less than 1, 0.5, 0.1 or 0.03 percent by weight of didehydro zolmitriptan.

Typically, the particles of the delivered condensation aerosol have a mass median aerodynamic diameter of less than 5 microns. Preferably, the particles have a mass median aerodynamic diameter of less than 3 microns. More preferably, the particles have a mass median aerodynamic diameter of less than 2 or 1 micron(s).

Typically, the geometric standard deviation around the mass median aerodynamic diameter of the aerosol particles is less than 3.5. Preferably, the geometric standard deviation is less than 3.0. More preferably, the geometric standard deviation is less than 2.5 or 2.0.

Typically, the delivered aerosol has an inhaleable aerosol drug mass density of between 0.25 mg/L and 40 mg/L. Preferably, the aerosol has an inhaleable drug mass density of between 0.5 mg/L and 20 mg/L. More preferably, the aerosol has an inhalable drug mass density of between 0.5 mg/L and 10 mg/L.

Typically, the delivered aerosol has an inhalable aerosol particle density greater than $10^6$ particles/mL. Preferably, the aerosol has an inhalable aerosol particle density greater than $10^7$ particles/mL or $10^8$ particles/mL.

Typically, the rate of inhalable aerosol particle formation of the delivered condensation aerosol is greater than $10^8$ particles per second. Preferably, the aerosol is formed at a rate greater than $10^9$ inhaleable particles per second. More preferably, the aerosol is formed at a rate greater than $10^{10}$ inhaleable particles per second.

Typically, the delivered condensation aerosol is formed at a rate greater than 0.5 mg/second. Preferably, the aerosol is formed at a rate greater than 0.75 mg/second. More preferably, the aerosol is formed at a rate greater than 1 mg/second, 1.5 mg/second or 2 mg/second.

Typically, where the condensation aerosol comprises rizatriptan, between 1 mg and 20 mg of rizatriptan are delivered to the mammal in a single inspiration. Preferably, between 1.5 mg and 15 mg of rizatriptan are delivered to the mammal in a single inspiration. More preferably, between 2 mg and 10 mg of rizatriptan are delivered to the mammal in a single inspiration.

Typically, where the condensation aerosol comprises zolmitriptan, between 0.5 mg and 10 mg of zolmitriptan are delivered to the mammal in a single inspiration. Preferably, between 1.5 mg and 7.5 mg of zolmitriptan are delivered to the mammal in a single inspiration. More preferably, between 2 mg and 5 mg of zolmitriptan are delivered to the mammal in a single inspiration.

Typically, the delivered condensation aerosol results in a peak plasma concentration of rizatriptan or zolmitriptan in the mammal in less than 1 h. Preferably, the peak plasma concentration is reached in less than 0.5 h. More preferably, the peak plasma concentration is reached in less than 0.2, 0.1, 0.05, 0.02, 0.01, or 0.005 h (arterial measurement).

Typically, the delivered condensation aerosol is used to treat migraine.

Typically, where the condensation aerosol comprises rizatriptan, less than 4 mg of rizatriptan is inhaled by the mammal in a 2 hour period. Preferably, less than 3.5 mg of rizatriptan is inhaled by the mammal in a 2 hour period. More preferably, less than 3.0 or 2.5 mg of rizatriptan is inhaled by the mammal in a 2 hour period.

Typically, where the condensation aerosol comprises zolmitriptan, less than 1 mg of zolmitriptan is inhaled by the mammal in a 2 hour period. Preferably, less than 0.75 mg of zolmitriptan is inhaled by the mammal in a 2 hour period. More preferably, less than 0.5 mg of zolmitriptan is inhaled by the mammal in a 2 hour period.

In another method aspect of the present invention, a method of treating migraine is provided which comprises administering a dose of an antimigraine compound to a mammal that is less than the typical oral dose.

Typically, where the antimigraine compound is rizatriptan, less than 4 mg of rizatriptan is administered to the mammal in any 2 hour period. Preferably, less than 3.5 mg of rizatriptan is administered to the mammal in any 2 hour period. More preferably, less than 3.0 mg or 2.5 mg of rizatriptan is administered to the mammal in any 2 hour period.

Typically, where the antimigraine compound is zolmitriptan, less than 1 mg of zolmitriptan is administered to the mammal in any 2 hour period. Preferably, less than 0.75 mg of zolmitriptan is administered to the mammal in any 2 hour period. More preferably, less than 0.5 mg of zolmitriptan is administered to the mammal in any 2 hour period.

In a kit aspect of the present invention, a kit for delivering rizatriptan or zolmitriptan through an inhalation route to a mammal is provided which comprises: a) a composition comprising at least 5 percent by weight of rizatriptan and zolmitriptan; and, b) a device that forms a rizatriptan or zolmitriptan aerosol from the composition, for inhalation by the mammal. Preferably, the composition comprises at least 20 percent, 30 percent, 40 percent, 50 percent, 60 percent, 70 percent, 80 percent, 90 percent, 95 percent, 97 percent, 99 percent, 99.5 percent, 99.9 percent or 99.97 percent by weight of rizatriptan or zolmitriptan.

Typically, the device contained in the kit comprises: a) an element for heating the rizatriptan or zolmitriptan composition to form a vapor; b) an element allowing the vapor to cool to form an aerosol; and, c) an element permitting the mammal to inhale the aerosol.

Typically, where the kit comprises rizatriptan, it comprises less than 4 mg of rizatriptan. Preferably, the kit comprises less than 3.5 mg of rizatriptan. More preferably, it comprises less than 3 mg or 2.5 mg of rizatriptan.

Typically, where the kit comprises zolmitriptan, it comprises less than 1 mg of zolmitriptan. Preferably, the kit comprises less than 0.75 mg of zolmitriptan. More preferably, it comprises less than 0.5 mg of zolmitriptan.

DETAILED DESCRIPTION OF THE INVENTION

Definitions

Figure 1:
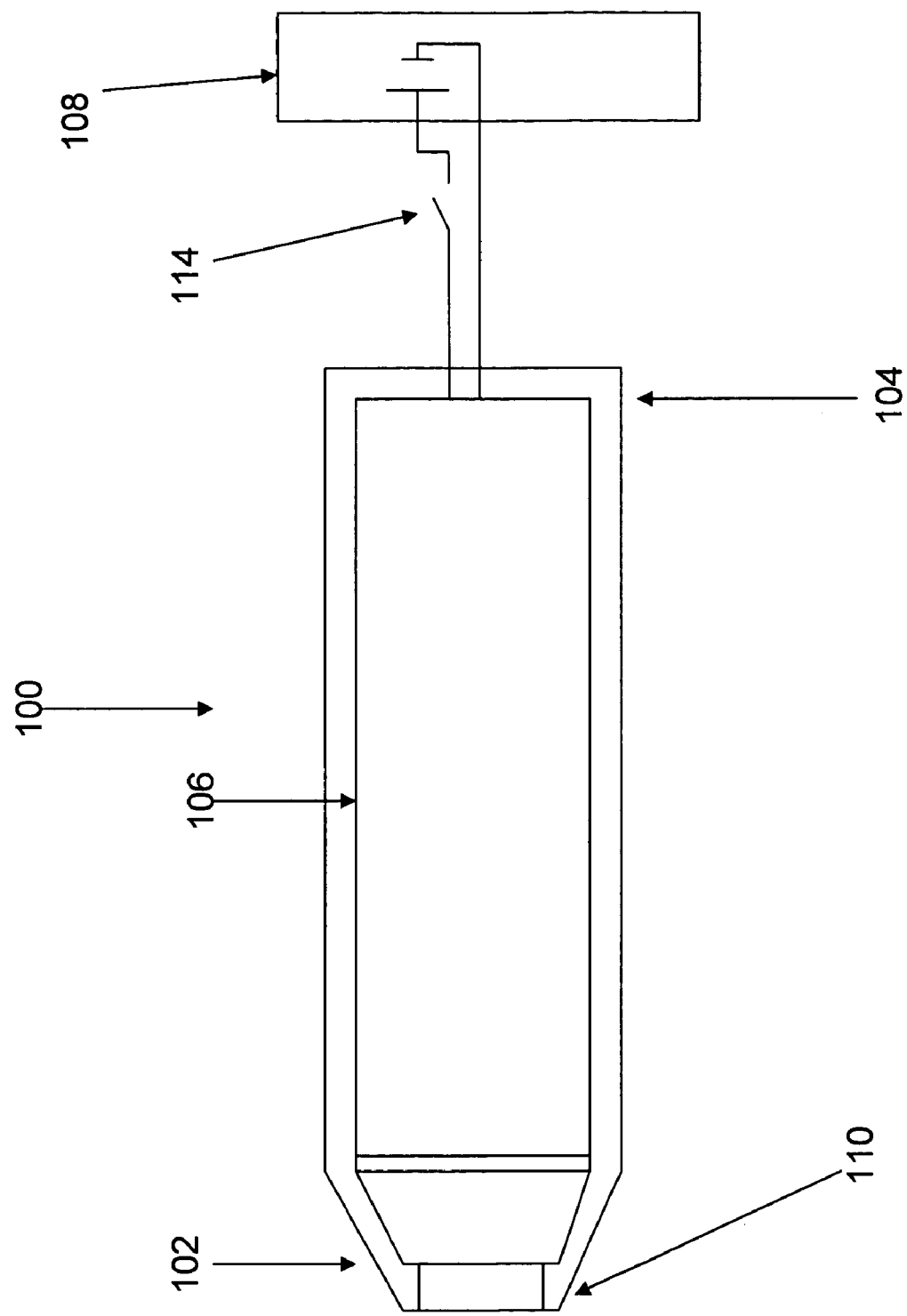
FIG. 1 shows a cross-sectional view of a device used to deliver rizatriptan or zolmitriptan containing aerosols to a mammal through an inhalation route.

"Aerodynamic diameter" of a given particle refers to the diameter of a spherical droplet with a density of 1 g/mL (the density of water) that has the same settling velocity as the given particle.

"Aerosol" refers to a suspension of solid or liquid particles in a gas.

"Aerosol drug mass density" refers to the mass of rizatriptan or zolmitriptan per unit volume of aerosol.

"Aerosol mass density" refers to the mass of particulate matter per unit volume of aerosol.

"Aerosol particle density" refers to the number of particles per unit volume of aerosol.

"Amorphous particle" refers to a particle that does not contain more than 50 percent by weight of a crystalline form. Preferably, the particle does not contain more than 25 percent by weight of a crystalline form. More preferably, the particle does not contain more than 10 percent by weight of a crystalline form.

"Condensation aerosol" refers to an aerosol formed by vaporization of a substance followed by condensation of the substance into an aerosol.

"Inhalable aerosol drug mass density" refers to the aerosol drug mass density produced by an inhalation device and delivered into a typical patient tidal volume.

"Inhalable aerosol mass density" refers to the aerosol mass density produced by an inhalation device and delivered into a typical patient tidal volume.

"Inhalable aerosol particle density" refers to the aerosol particle density of particles of size between 100 nm and 5 microns produced by an inhalation device and delivered into a typical patient tidal volume.

"Mass median aerodynamic diameter" or "MMAD" of an aerosol refers to the aerodynamic diameter for which half the particulate mass of the aerosol is contributed by particles with an aerodynamic diameter larger than the MMAD and half by particles with an aerodynamic diameter smaller than the MMAD.

"Rate of aerosol formation" refers to the mass of aerosolized particulate matter produced by an inhalation device per unit time.

"Rate of inhalable aerosol particle formation" refers to the number of particles of size between 100 nm and 5 microns produced by an inhalation device per unit time.

"Rate of drug aerosol formation" refers to the mass of aerosolized rizatriptan or zolmitriptan produced by an inhalation device per unit time.

"Rizatriptan" refers to N,N-dimethyl-5-(1H-1,2,4-triazol-1-ylmethyl)-1H-indole-3-ethanamine, which has an empirical formula of $C_{15}H_{19}N_5$. The compound is a free base with a molecular weight of 269.4 g/m.

"Rizatriptan degradation product" refers to a compound resulting from a chemical modification of rizatriptan. The modification, for example, can be the result of a thermally or photochemically induced reaction. Such reactions include, without limitation, oxidation (e.g., N-oxide formation), elimination (e.g., $E_1$ and $E_2$ reaction pathways) and dimerization.

"Settling velocity" refers to the terminal velocity of an aerosol particle undergoing gravitational settling in air.

"Typical patient tidal volume" refers to 1 L for an adult patient and 15 mL/kg for a pediatric patient.

"Vapor" refers to a gas, and "vapor phase" refers to a gas phase. The term "thermal vapor" refers to a vapor phase, aerosol, or mixture of aerosol-vapor phases, formed preferably by heating.

"Zolmitriptan" refers to (S)-4-[[3-[2-(dimethylamino) ethyl]-1H-indol-5-yl]methyl]-2-oxazolidinone, which has an empirical formula of $C_{16}H_{21}N_3O_2$. The compound is a free base with a molecular weight of 287.36 g/m.

"Zolmitriptan degradation product" refers to a compound resulting from a chemical modification of zolmitriptan. The modification, for example, can be the result of a thermally or photochemically induced reaction. Such reactions include, without limitation, oxidation (e.g., N-oxide formation), elimination (e.g., $E_1$ and $E_2$ reaction pathways) and dimerization.

Obtaining Rizatriptan or Zolmitriptan

Rizatriptan and zolmitriptan are either isolated from commercially available products or synthesized. To isolate rizatriptan, MAXALT® Tablets are dissolved in water and treated with base to form rizatriptan free base. The free base is extracted with diethyl ether to afford rizatriptan. Zolmitriptan is isolated by dissolving ZOMIG® Tablets in water and extracting the aqueous solution with diethyl ether and dichloromethane.

Synthetic routes to both rizatriptan and zolmitriptan are well known. U.S. Pat. No. 5,298,520, for instance, describes the synthesis of rizatriptan. The synthesis of zolmitriptan is reported in U.S. Pat. No. 5,399,574.

Formation of Rizatriptan or Zolmitriptan Containing Aerosols

Any suitable method is used to form the aerosols of the present invention. A preferred method, however, involves heating a composition comprising rizatriptan or zolmitriptan to form a vapor, followed by cooling of the vapor such that it condenses to provide a rizatriptan or zolmitriptan comprising aerosol (condensation aerosol). The composition is heated in one of four forms: as pure active compound (i.e., pure rizatriptan or zolmitriptan); as a mixture of active compound and a pharmaceutically acceptable excipient; as a salt form of the pure active compound; and, as a mixture of active compound salt form and a pharmaceutically acceptable excipient.

Salt forms of rizatriptan or zolmitriptan are either commercially available or are obtained from the corresponding free base using well known methods in the art. A variety of pharmaceutically acceptable salts are suitable for aerosolization. Such salts include, without limitation, the following: hydrochloric acid, hydrobromic acid, acetic acid, maleic acid, formic acid, and fumaric acid salts.

Pharmaceutically acceptable excipients may be volatile or nonvolatile. Volatile excipients, when heated, are concurrently volatilized, aerosolized and inhaled with rizatriptan or zolmitriptan. Classes of such excipients are known in the art and include, without limitation, gaseous, supercritical fluid, liquid and solid solvents. The following is a list of exemplary carriers within the classes: water; terpenes, such as menthol; alcohols, such as ethanol, propylene glycol, glycerol and other similar alcohols; dimethylformamide; dimethylacetamide; wax; supercritical carbon dioxide; dry ice; and mixtures thereof.

Solid supports on which the composition is heated are of a variety of shapes. Examples of such shapes include, without limitation, cylinders of less than 1.0 mm in diameter, boxes of less than 1.0 mm thickness and virtually any shape permeated by small (e.g., less than 1.0 mm-sized) pores. Preferably, solid supports provide a large surface to volume ratio (e.g., greater than 100 per meter) and a large surface to mass ratio (e.g., greater than 1 $cm^2$ per gram).

A solid support of one shape can also be transformed into another shape with different properties. For example, a flat sheet of 0.25 mm thickness has a surface to volume ratio of approximately 8,000 per meter. Rolling the sheet into a hollow cylinder of 1 cm diameter produces a support that retains the high surface to mass ratio of the original sheet but has a lower surface to volume ratio (about 400 per meter).

A number of different materials are used to construct the solid supports. Classes of such materials include, without limitation, metals, inorganic materials, carbonaceous materials and polymers. The following are examples of the material classes: aluminum, silver, gold, stainless steel, copper and tungsten; silica, glass, silicon and alumina; graphite, porous carbons, carbon yarns and carbon felts; polytetrafluoroethylene and polyethylene glycol. Combinations of materials and coated variants of materials are used as well.

Where aluminum is used as a solid support, aluminum foil is a suitable material. Examples of silica, alumina and silicon based materials include amphorous silica S-5631 (Sigma, St. Louis, Mo.), BCR171 (an alumina of defined surface area greater than 2 $m^2$/g from Aldrich, St. Louis, Mo.) and a silicon wafer as used in the semiconductor industry. Carbon yarns and felts are available from American Kynol, Inc., New York, N.Y. Chromatography resins such as octadecycl silane chemically bonded to porous silica are exemplary coated variants of silica.

The heating of the rizatriptan or zolmitriptan compositions is performed using any suitable method. Examples of methods by which heat can be generated include the following: passage of current through an electrical resistance element; absorption of electromagnetic radiation, such as microwave or laser light; and, exothermic chemical reactions, such as exothermic salvation, hydration of pyrophoric materials and oxidation of combustible materials.

Delivery of Rizatriptan or Zolmitriptan Containing Aerosols

Rizatriptan or zolmitriptan containing aerosols of the present invention are delivered to a mammal using an inhalation device. Where the aerosol is a condensation aerosol, the device has at least three elements: an element for heating a rizatriptan or zolmitriptan containing composition to form a vapor; an element allowing the vapor to cool, thereby providing a condensation aerosol; and, an element permitting the mammal to inhale the aerosol. Various suitable heating methods are described above. The element that allows cooling is, in it simplest form, an inert passageway linking the heating means to the inhalation means. The element permitting inhalation is an aerosol exit portal that forms a connection between the cooling element and the mammal's respiratory system.

One device used to deliver the rizatriptan or zolmitriptan containing aerosol is described in reference to FIG. 1. Delivery device 100 has a proximal end 102 and a distal end 104, a heating module 106, a power source 108, and a mouthpiece 110. A rizatriptan or zolmitriptan composition is deposited on a surface 112 of heating module 106. Upon activation of a user activated switch 114, power source 108 initiates heating of heating module 106 (e.g, through ignition of combustible fuel or passage of current through a resistive heating element). The rizatriptan or zolmitriptan composition volatilizes due to the heating of heating module 106 and condenses to form a condensation aerosol prior to reaching the mouthpiece 110 at the proximal end of the device 102. Air flow travelling from the device distal end 104 to the mouthpiece 110 carries the condensation aerosol to the mouthpiece 110, where it is inhaled by the mammal.

Devices, if desired, contain a variety of components to facilitate the delivery of rizatriptan or zolmitriptan containing aerosols. For instance, the device may include any component known in the art to control the timing of drug aerosolization relative to inhalation (e.g., breath-actuation), to provide feedback to patients on the rate and/or volume of inhalation, to prevent excessive use (i.e., "lock-out" feature), to prevent use by unauthorized individuals, and/or to record dosing histories.

Dosage of Rizatriptan or Zolmitrip tan Containing Aerosols

Rizatriptan and zolmitriptan are given orally at strengths of 5 mg or 10 mg and 2.5 mg or 5 mg respectively for the treatment of migraine. As aerosols, 0.5 mg to 15 mg of rizatriptan and 0.25 mg to 7.5 mg of zolmitriptan are generally provided per inspiration for the same indication. A typical dosage of a rizatriptan or zolmitriptan aerosol is either administered as a single inhalation or as a series of inhalations taken within an hour or less (dosage equals sum of inhaled amounts). Where the drug is administered as a series of inhalations, a different amount may be delivered in each inhalation. The dosage amount of rizatriptan or zolmitriptan in aerosol form is generally no greater than twice the standard dose of the drug given orally.

One can determine the appropriate dose of rizatriptan or zolmitriptan containing aerosols to treat a particular condition using methods such as animal experiments and a dose-finding (Phase I/II) clinical trial. One animal experiment involves measuring plasma concentrations of drug in an animal after its exposure to the aerosol. Mammals such as dogs or primates are typically used in such studies, since their respiratory systems are similar to that of a human. Initial dose levels for testing in humans is generally less than or equal to the dose in the mammal model that resulted in plasma drug levels associated with a therapeutic effect in humans. Dose escalation in humans is then performed, until either an optimal therapeutic response is obtained or a dose-limiting toxicity is encountered.

Analysis of Rizatriptan or Zolmitriptan Containing Aerosols

Purity of a rizatriptan or zolmitriptan containing aerosol is determined using a number of methods, examples of which are described in Sekine et al., *Journal of Forensic Science* 32:1271–1280 (1987) and Martin et al., *Journal of Analytic Toxicology* 13:158–162 (1989). One method involves forming the aerosol in a device through which a gas flow (e.g., air flow) is maintained, generally at a rate between 0.4 and 60 L/min. The gas flow carries the aerosol into one or more traps. After isolation from the trap, the aerosol is subjected to an analytical technique, such as gas or liquid chromatography, that permits a determination of composition purity.

A variety of different traps are used for aerosol collection. The following list contains examples of such traps: filters; glass wool; impingers; solvent traps, such as dry ice-cooled ethanol, methanol, acetone and dichloromethane traps at various pH values; syringes that sample the aerosol; empty, low-pressure (e.g., vacuum) containers into which the aerosol is drawn; and, empty containers that fully surround and enclose the aerosol generating device. Where a solid such as glass wool is used, it is typically extracted with a solvent such as ethanol. The solvent extract is subjected to analysis rather than the solid (i.e., glass wool) itself. Where a syringe or container is used, the container is similarly extracted with a solvent.

The gas or liquid chromatograph discussed above contains a detection system (i.e., detector). Such detection systems are well known in the art and include, for example, flame ionization, photon absorption and mass spectrometry detectors. An advantage of a mass spectrometry detector is that it can be used to determine the structure of rizatriptan or zolmitriptan degradation products.

Particle size distribution of a rizatriptan or zolmitriptan containing aerosol is determined using any suitable method in the art (e.g., cascade impaction). An Andersen Eight Stage Non-viable Cascade Impactor (Andersen Instruments, Smyrna, Ga.) linked to a furnace tube by a mock throat (USP throat, Andersen Instruments, Smyrna, Ga.) is one system used for cascade impaction studies.

Inhalable aerosol mass density is determined, for example, by delivering a drug-containing aerosol into a confined chamber via an inhalation device and measuring the mass collected in the chamber. Typically, the aerosol is drawn into the chamber by having a pressure gradient between the device and the chamber, wherein the chamber is at lower pressure than the device. The volume of the chamber should approximate the tidal volume of an inhaling patient.

Inhalable aerosol drug mass density is determined, for example, by delivering a drug-containing aerosol into a confined chamber via an inhalation device and measuring the amount of active drug compound collected in the chamber. Typically, the aerosol is drawn into the chamber by having a pressure gradient between the device and the chamber, wherein the chamber is at lower pressure than the device. The volume of the chamber should approximate the tidal volume of an inhaling patient. The amount of active drug compound collected in the chamber is determined by extracting the chamber, conducting chromatographic analysis of the extract and comparing the results of the chromatographic analysis to those of a standard containing known amounts of drug.

Inhalable aerosol particle density is determined, for example, by delivering aerosol phase drug into a confined chamber via an inhalation device and measuring the number of particles of given size collected in the chamber. The number of particles of a given size may be directly measured based on the light-scattering properties of the particles. Alternatively, the number of particles of a given size is determined by measuring the mass of particles within the given size range and calculating the number of particles based on the mass as follows: Total number of particles=Sum (from size range 1 to size range N) of number of particles in each size range. Number of particles in a given size range=Mass in the size range/Mass of a typical particle in the size range. Mass of a typical particle in a given size range=$\pi * D^3 * \phi/6$, where D is a typical particle diameter in the size range (generally, the mean boundary MMADs defining the size range) in microns, $\phi$ is the particle density (in g/mL) and mass is given in units of picograms ($g^{-12}$).

Rate of inhalable aerosol particle formation is determined, for example, by delivering aerosol phase drug into a confined chamber via an inhalation device. The delivery is for a set period of time (e.g., 3 s), and the number of particles of a given size collected in the chamber is determined as outlined above. The rate of particle formation is equal to the number of 100 nm to 5 micron particles collected divided by the duration of the collection time.

Rate of aerosol formation is determined, for example, by delivering aerosol phase drug into a confined chamber via an inhalation device. The delivery is for a set period of time (e.g., 3 s), and the mass of particulate matter collected is determined by weighing the confined chamber before and after the delivery of the particulate matter. The rate of aerosol formation is equal to the increase in mass in the chamber divided by the duration of the collection time. Alternatively, where a change in mass of the delivery device or component thereof can only occur through release of the aerosol phase particulate matter, the mass of particulate matter may be equated with the mass lost from the device or component during the delivery of the aerosol. In this case, the rate of aerosol formation is equal to the decrease in mass of the device or component during the delivery event divided by the duration of the delivery event.

Rate of drug aerosol formation is determined, for example, by delivering a rizatriptan or zolmitriptan containing aerosol into a confined chamber via an inhalation device over a set period of time (e.g., 3 s). Where the aerosol is pure rizatriptan or zolmitriptan, the amount of drug collected in the chamber is measured as described above. The rate of drug aerosol formation is equal to the amount of rizatriptan or zolmitriptan collected in the chamber divided by the duration of the collection time. Where the rizatriptan or zolmitriptan containing aerosol comprises a pharmaceutically acceptable excipient, multiplying the rate of aerosol formation by the percentage of rizatriptan or zolmitriptan in the aerosol provides the rate of drug aerosol formation.

Utility of Rizatriptan or Zolmitriptan Containing Aerosols

Rizatriptan and Zolmitriptan are selective 5-HT$_1$ subtype agonists. Such compounds exhibit vasoconstrictor activity and are used for the treatment of headache. Examples of headaches that are treated by administration of rizatriptan or zolmitriptan include migraine, cluster headache, chronic paroxysmal hemicrania, headache associated with vascular disorders, tension headaches and pediatric migraine.

The following examples are meant to illustrate, rather than limit, the present invention.

EXAMPLE 1

Isolation of Rizatriptan

To 10 mL of water was added 9 MAXALT® Tablets, each containing 10 mg of rizatriptan. After the tablets dissolved, 1N NaOH was added to the solution until it became basic (pH 11-12). The aqueous solution was extracted six times with diethyl ether. The combined ether extracts were dried (Na$_2$SO$_4$), filtered and concentrated on a rotary evaporator to provide 88 mg (98% recovery) of rizatriptan.

EXAMPLE 2

Volatilization of Rizatriptan

A solution of 10 mg rizatriptan in 1 mL diethyl ether was spread out in a thin layer on a 10 cm x 15 cm sheet of aluminum foil. The diethyl ether was allowed to evaporate. Assuming a drug density of about 1 g/cc. the calculated thickness of the rizatriptan coating on the 150 cm$^2$ aluminum solid support after solvent evaporation, is about 0.7 microns. The coated aluminum foil sheet was inserted into a glass tube in a furnace (tube furnace). A glass wool plug was placed in the tube adjacent to the foil sheet, and an air flow of 2 L/min was applied. The furnace was heated to 250 ° C. for 30 s to volatilize the coated rizatriptan and then was allowed to cool. The glass wool was extracted, and HPLC analysis of the collected material showed it to be at least 99% pure rizatriptan.

EXAMPLE 3

Particle Size, Particle Density, and Rate of Inhalable Particle Formation of Rizatriptan Aerosol A solution of 11.3 mg rizatriptan in 200 μL dichloromethane was spread out in a thin layer on the central portion of a 4 cm x 9 cm sheet of aluminum foil. The dichloromethane was allowed to evaporate. Assuming a drug density of about 1 g/cc. the calculated thickness of the rizatriptan thin layer on the 36 cm$^2$ aluminum solid support, after solvent evaporation, is about 3.1 microns. The aluminum foil was wrapped around a 300 watt halogen tube, which was inserted into a T-shaped glass tube. One of the openings of the tube was sealed with a rubber stopper, another was loosely covered with the end of the halogen tube, and the third, was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 7 s. The aerosol was analyzed by connecting the 1 L flask to an eight-stage Andersen non-viable cascade impactor. Results are shown in table 1. MMAD of the collected aerosol was 1.2 microns with a geometric standard deviation of 1.7. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^{3/6}$, multiplied by the density of the drug (taken to be 1 g/cm$^3$). The inhalable aerosol particle density is the sum of the numbers of particles collected on impactor stages 3 to 8 divided by the collection volume of I L, giving an inhalable aerosol particle density of 3 ×10$^7$ particles/mL. The rate of inhalable aerosol particle formation is the sum of the numbers of particles collected on impactor stages 3 through 8 divided by the formation time of 7 s, giving a rate of inhalable aerosol particle formation of 5 ×10$^9$ particles/second.

TABLE 1

Determination of the characteristics of a rizatriptan condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.0 | 0 |
| 1 | 5.8–9.0 | 7.4 | 0.0 | 0 |
| 2 | 4.7–5.8 | 5.25 | 0.1 | 1.3 × 10$^6$ |
| 3 | 3.3–4.7 | 4.0 | 0.2 | 6.0 × 10$^6$ |
| 4 | 2.1–3.3 | 2.7 | 0.4 | 3.9 × 10$^7$ |
| 5 | 1.1–2.1 | 1.6 | 1.2 | 5.6 × 10$^8$ |

TABLE 1-continued

Determination of the characteristics of a rizatriptan condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 6 | 0.7–1.1 | 0.9 | 1.0 | $2.6 \times 10^9$ |
| 7 | 0.4–0.7 | 0.55 | 0.5 | $5.7 \times 10^9$ |
| 8 | 0–0.4 | 0.2 | 0.1 | $2.4 \times 10^{10}$ |

EXAMPLE 4

Drug Mass Density and Rate of Drug Aerosol Formation of Rizatriptan Aerosol

A solution of 11.6 mg rizatriptan in 200 µL dichloromethane was spread out in a thin layer on the central portion of a 4 cm x 9 cm sheet of aluminum foil. The dichloromethane was allowed to evaporate. Assuming a drug density of about 1 g/cc. the calculated thickness of the rizatriptan thin layer on the 36 cm² aluminum solid support after solvent evaporation, is about 3.2 microns. The aluminum foil was wrapped around a 300 watt halogen tube, which was inserted into a T-shaped glass tube. One of the openings of the tube was sealed with a rubber stopper, another was loosely covered with the end of the halogen tube, and the third was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 7 s. The aerosol was allowed to sediment onto the walls of the 1 L flask for approximately 30 minutes. The flask was then extracted with dichloromethane and the extract analyzed by HPLC with detection by light absorption at 225 nm. Comparison with standards containing known amounts of rizatriptan revealed that 3.2 mg of >99% pure rizatriptan had been collected in the flask, resulting in an aerosol drug mass density of 3.2 mg/L. The aluminum foil upon which the rizatriptan had previously been coated was weighed following the experiment. Of the 11.6 mg originally coated on the aluminum, all of the material was found to have aerosolized in the 7 s time period, implying a rate of drug aerosol formation of 1.7 mg/s.

EXAMPLE 5

Isolation of Zolmitriptan

To water was added 17 ZOMIG® Tablets, each containing 5 mg of zolmitriptan. The resulting milky solution was extracted three times with diethyl ether and three times with dichloromethane. The combined organic extracts were dried (MgSO$_4$), filtered and concentrated on a rotary evaporator to provide 100 mg (74% recovery) of zolmitriptan.

EXAMPLE 7

Particle Size, Particle Density, and Rate of Inhalable Particle Formation of Zohnitriptan Aerosol A solution of 3.2 mg zolmitriptan in 100 µL methanol was spread out in a thin layer on the central portion of a 3.5 cm×7 cm sheet of aluminum foil. The dichloromethane was allowed to evaporate. Assuming a drug density of about 1 g/cc. the calculated thickness of the zolmitriptan thin layer on the 24.5 cm² aluminum solid support, after solvent evaporation, is about 1.3 microns. The aluminum foil was wrapped around a 300 watt halogen tube, which was inserted into a T-shaped glass tube. Both of the openings of the tube were left open and the third opening was connected to a l liter, 3-neck glass flask. The glass flask was further connected to a large piston capable of drawing 1.1 liters of air through the flask. Alternating current was run through the halogen bulb by application of 90 V using a variac connected to 110 V line power. Within 1 s, an aerosol appeared and was drawn into the 1 L flask by use of the piston, with collection of the aerosol terminated after 6 s. The aerosol was analyzed by connecting the 1 L flask to an eight-stage Andersen non-viable cascade impactor. Results are shown in table 1. MMAD of the collected aerosol was 0.7 microns with a geometric standard deviation of 3.3. Also shown in table 1 is the number of particles collected on the various stages of the cascade impactor, given by the mass collected on the stage divided by the mass of a typical particle trapped on that stage. The mass of a single particle of diameter D is given by the volume of the particle, $\pi D^3/6$, multiplied by the density of the drug (taken to be 1 g/cm³). The inhalable aerosol particle density is the sum of the numbers of particles collected on impactor stages 3 to 8 divided by the collection volume of 1 L, giving an inhalable aerosol particle density of $4.9 \times 10^7$ particles/mL. The rate of inhalable aerosol particle formation is the sum of the numbers of particles collected on impactor stages 3 through 8 divided by the formation time of 6 s, giving a rate of inhalable aerosol particle formation of $8.1 \times 10^9$ particles/second.

TABLE 1

Determination of the characteristics of a zolmitriptan condensation aerosol by cascade impaction using an Andersen 8-stage non-viable cascade impactor run at 1 cubic foot per minute air flow.

| Stage | Particle size range (microns) | Average particle size (microns) | Mass collected (mg) | Number of particles |
|---|---|---|---|---|
| 0 | 9.0–10.0 | 9.5 | 0.00 | 0 |
| 1 | 5.8–9.0 | 7.4 | 0.00 | 0 |
| 2 | 4.7–5.8 | 5.25 | 0.00 | 0 |
| 3 | 3.3–4.7 | 4.0 | 0.01 | $2.1 \times 10^5$ |
| 4 | 2.1–3.3 | 2.7 | 0.03 | $2.9 \times 10^6$ |
| 5 | 1.1–2.1 | 1.6 | 0.12 | $5.7 \times 10^7$ |
| 6 | 0.7–1.1 | 0.9 | 0.10 | $2.5 \times 10^8$ |
| 7 | 0.4–0.7 | 0.55 | 0.05 | $5.7 \times 10^8$ |
| 8 | 0–0.4 | 0.2 | 0.20 | $4.8 \times 10^{10}$ |

EXAMPLE 6

Vaporization of Zolmitriptan

A solution of 9.8 mg zolmitriptan in 300 µL dichloromethane was spread out in a thin layer on a 4 cm x 9 cm sheet of aluminum foil. The dichloromethane was allowed to evaporate. Assuming a drug density of about 1 a/cc. the calculated thickness of the zolmitriptan thin layer on the 36 cm² aluminum solid support, after solvent evaporation, is about 2.7 microns. The aluminum foil was wrapped around a 300 watt halogen tube, which was inserted into a glass tube sealed at one end with a rubber stopper. Subjecting the bulb to one 15s, 60 v (variac) treatment afforded volatilized zolmitriptan on the glass tube walls. HPLC analysis of the collected material showed it to be at least 98% pure zolmitriptan. To obtain higher purity aerosols, one can coat a lesser amount of drug, yielding a thinner film to heat. A linear decrease in film thickness is associated with a linear decrease in impurities.

EXAMPLE 8

Drug Mass Density and Rate of Drug Aerosol Formation of Zolmitriptan Aerosol A solution of 2.6 mg zolmitriptan in 100 µL methanol was spread out in a thin layer on the central portion of a 3.5 cm×7 cm sheet of aluminum foil. The dichloromethane was allowed to evaporate. Assuming a drug density of about 1 g/cc. the calculated thickness of the zolmitriptan thin layer on the 24.5 cm² aluminum solid support after solvent evaporation is about 1.1 microns. The aluminum foil was wrapped around a 300 watt halogen tube, which was inserted into a T-shaped glass tube. Both of the openings of the tube were left open and the third opening was connected to a 1 liter, 3-neck glass flask. The glass flask was further connected to a large piston capable of drawing 1.1 liters of air through the flask. Alternating current was run through the halogen bulb by application of 90 V using a variac connected to 110 V line power. Within seconds, an aerosol appeared and was drawn into the 1 L flask by use of the piston, with formation of the aerosol terminated after 6 s. The aerosol was allowed to sediment onto the walls of the 1 L flask for approximately 30 minutes. The flask was then extracted with acetonitrile and the extract analyzed by HPLC with detection by light absorption at 225 nm. Comparison with standards containing known amounts of zolmitriptan revealed that 0.4 mg of >96% pure zolmitriptan had been collected in the flask, resulting in an aerosol drug mass density of 0.4 mg/L. The aluminum foil upon which the zolmitriptan had previously been coated was weighed following the experiment. Of the 2.6 mg originally coated on the aluminum, 1.5 mg of the material was found to have aerosolized in the 6 s time period, implying a rate of drug aerosol formation of 0.3 mg/s.

EXAMPLE 9

Flash Device for Forming Aerosols

A high-power flashcube (GE or Sylvania), which can produce 300–400 J of energy, was inserted into an anodized aluminum tube. The flashcube/tube assembly was dipped into an organic solution containing a drug and quickly removed. Evaporation of residual solvent from the assembly was performed by placing it into a vacuum chamber for 30 min. This left a film of drug coated on the exterior surface of the aluminum tube. The flashbulb assembly was electrically connected to two 1.5 V batteries and a switch using copper wires and then enclosed in a sealed, glass vial. Ignition of the flashbulb was performed by momentarily turning on the switch between the flashbulb and batteries. After ignition, the vial was kept closed for 30 minutes such that particles of volatilized drug coagulated and condensed on the inside surface of the vial. Analysis of the aerosol involved rinsing the vial with 5 mL of acetonitrile and injecting a sample of the organic solution into an HPLC. Rizatriptan aerosol was obtained in 99.2% purity (1.65 mg) using this procedure. Zolmitriptan aerosol was obtained in 99.6% purity (0.31 mg) using this procedure.

EXAMPLE 10

Delivery of Rizatriptan to a Dog

Apnea was induced in a dog, which was subsequently exposed to a 15 SLPM flow of air containing 950 µg of rizatriptan (condensation aerosol formed by volatilizing triazolam off of a heated, metal substrate; MMAD ~1.7) through an endotracheal tube. This corresponded to approximately a 625 cc volume of inhalation air delivered to the dog. Once the dog had received the triazolam aerosol, an air supply valve was shut off for 5 s, which simulated a 5 s breath hold. Following the hold, the dog was allowed to exhale through an exhalation filter. Arterial blood samples were taken at defined intervals. HPLC analysis of the blood samples indicated that the Tmax for rizatriptan was about 1 minutes, with a concentration of greater than 280 ng/mL reached.

EXAMPLE 11

Comparison of Inhaled, Subcutaneous and Oral Admistration of Rizatriptan in a Dog The percent change in cerebral vascular resistance from a 30 minute baseline was compared after administration of 1 mg of rizatriptan to a dog using the following delivery routes: inhalation, subcutaneous, and oral. After inhalation administration, the resistance increased approximately 60 percent in approximately 1 minute. Subcutaneous administration produced about a 45 percent increase in resistance in about 20 minutes. Cerebral vascular resistance essentially did not change over an 80 minute period after oral administration of rizatriptan.

The same study was performed by administering either 3.5 mg or 3 mg of rizatriptan to a dog: inhalation (3.5 mg inhaled, ~110% resistance increase in about one minute); subcutaneous (3 mg, ~60% resistance increase over about 30 minutes); and, oral (3 mg, essentially no resistance increase over 80 min.).

The invention claimed is:

1. A dose form of rizatriptan comprising a condensation aerosol
    formed by heating a thin layer containing rizatriptan, on a solid support, to produce a vapor of rizatriptan and condensing the vapor to form a condensation aerosol characterized by less than 10% rizatriptan degradation products by weight, and
    an MMAD of less than 5 microns, wherein the dose form comprises less than 4 mg of rizatriptan.

2. A dose form of zolmitriptan comprising a condensation aerosol
    formed by heating a thin layer containing zolmitriptan, on a solid support, to produce a vapor of zolmitriptan and condensing the vapor to form a condensation aerosol characterized by less than 10% zolmitriptan degradation products by weight, and
    an MMAD of less than 5 microns, wherein the dose form comprises less than 1 mg zolmitriptan.

3. A method of producing a dose form of rizatriptan comprising a condensation aerosol, the method comprising:
  a. heating a thin layer containing rizatriptan, on a solid support, to produce a vapor of rizatriptan, and
  b. providing an air flow through the vapor to form a condensation aerosol characterized by less than 10% rizatriptan degradation products by weight, and an MMAD of less than 5 microns, wherein the dose form comprises less than 4 mg of rizatriptan.

4. A method of producing a dose form of zolmitriptan comprising a condensation aerosol, the method comprising:
  a. heating a thin layer containing zolmitriptan on a solid support, to produce a vapor of zolmitriptan, and
  b. providing an air flow through the vapor to form a condensation aerosol characterized by less than 10% zolmitriptan degradation products by weight, and an MMAD of less than 5 microns, wherein the dose form comprises less than 1 mg of zolmitriptan.

5. A condensation aerosol for delivery of rizatriptan, wherein the condensation aerosol is formed by heating a thin layer containing rizatriptan, on a solid support, to produce a vapor of rizatriptan and condensing the vapor to form a condensation aerosol characterized by less than 5% rizatriptan N-oxide or didehydro rizatriptan by weight, and an MMAD of less than 5 microns.

6. A condensation aerosol for delivery of zolmitriptan, wherein the condensation aerosol is formed by heating a thin layer containing zolmitriptan, on a solid support, to produce a vapor of zolmitriptan and condensing the vapor to form a condensation aerosol characterized by less than 5% zolmitriptan N-oxide or didehydro zolmitriptan by weight, and an MMAD of less than 5 microns.

7. A method of producing rizatriptan in an aerosol form comprising:
  a. heating a thin layer containing rizatriptan, on a solid support, to produce a vapor of rizatriptan, and
  b. providing an air flow thorough the vapor to form a condensation aerosol characterized by less than 5% rizatriptan N-oxide or didehydro rizatriptan by weight, and an MMAD of less than 5 microns.

8. A method of producing zolmitriptan in an aerosol form comprising:
  a. heating a thin layer containing zolmitriptan, on a solid support, to produce a vapor of zolmitriptan, and
  b. providing an air flow thorough the vapor to form a condensation aerosol characterized by less than 5% zolmitriptan N-oxide or didehydro zolmitriptan by weight, and an MMAD of less than 5 microns.

* * * * *